US011642236B2

(12) United States Patent
McKeown

(10) Patent No.: US 11,642,236 B2
(45) Date of Patent: *May 9, 2023

(54) NASAL BREATHING TRAINING TAPE AND METHOD

(71) Applicant: Patrick McKeown, County Galway (IE)

(72) Inventor: Patrick McKeown, County Galway (IE)

( * ) Notice: Subject to any disclaimer, the term of this patent is extended or adjusted under 35 U.S.C. 154(b) by 0 days.

This patent is subject to a terminal disclaimer.

(21) Appl. No.: 16/542,363

(22) Filed: Aug. 16, 2019

(65) Prior Publication Data
US 2021/0045909 A1 Feb. 18, 2021

(51) Int. Cl.
*A61F 5/37* (2006.01)
*A61F 5/56* (2006.01)
*A61M 16/06* (2006.01)

(52) U.S. Cl.
CPC ........... *A61F 5/37* (2013.01); *A61M 16/0688* (2014.02)

(58) Field of Classification Search
CPC .... A61F 5/37; A61F 5/3707; A61F 5/56–566; A61F 5/0003; A61F 5/0006; A61M 16/06; A61M 16/0605; A61M 16/0616; A61M 16/0683; A61M 16/0688; A45D 40/30; A45D 44/22
See application file for complete search history.

(56) References Cited

U.S. PATENT DOCUMENTS

| 2,695,622 | A | * | 11/1954 | Herod | A45D 40/30 |
| | | | | | 132/319 |
| 4,658,811 | A | * | 4/1987 | Beaird | A61F 5/56 |
| | | | | | 606/204.35 |
| 4,883,072 | A | | 11/1989 | Bessler | |

(Continued)

FOREIGN PATENT DOCUMENTS

| EP | 2517680 A2 * | 10/2012 | ......... A61F 13/0259 |
| JP | 2003159269 A | 6/2003 | |

(Continued)

OTHER PUBLICATIONS

Sleep Strips by SomniFix—Advanced Gentle Mouth Tape for Better Nose Breathing, Improved Nighttime Sleeping, Less Mouth Breathing, and Instant Snoring Relief, https://www.amazon.com/Sleep-Strips-SomniFix-Breathing-Nighttime/dp/B076CQ1NR8.

*Primary Examiner* — Michelle J Lee
(74) *Attorney, Agent, or Firm* — Sandy Lipkin

(57) ABSTRACT

Disclosed is a nasal breathing training tape adapted to impart training to a user to breathe from the nasal, and not from the mouth, during sleep time or wake-up time. The nasal breathing training tape includes a stretchable strip, an adhesive layer, and a cutout portion. The stretchable strip includes a first surface, and a second surface opposite to the first surface. The stretchable strip is stretchable to create tension therein. The adhesive layer may be applied to the second layer of the stretchable strip. The cutout portion is configured on the stretchable strip along a substantially central location of the stretchable strip. The stretchable strip is (Continued)

stretched up to a size to be accommodated and stick around a lip portion, surrounding the mouth but not touching the lip portion, of the user, such that the lip portion held together by the tension created in the stretchable strip.

7 Claims, 4 Drawing Sheets

(56) References Cited

U.S. PATENT DOCUMENTS

| | | | | |
|---|---|---|---|---|
| 5,640,974 | A * | 6/1997 | Miller | A61F 5/56 128/845 |
| 6,089,232 | A * | 7/2000 | Portnoy | A61F 5/56 128/859 |
| 6,123,082 | A * | 9/2000 | Berthon-Jones | A61M 16/06 128/857 |
| 9,433,740 | B2 | 9/2016 | Marcoe | |
| 2008/0041397 | A1 * | 2/2008 | Hirs | A61F 5/56 128/848 |
| 2010/0298861 | A1 * | 11/2010 | Fenton | A61F 5/08 606/199 |
| 2012/0136267 | A1 | 5/2012 | Derrick et al. | |
| 2014/0025102 | A1 * | 1/2014 | Lehman | A61F 5/56 606/204.45 |
| 2016/0302961 | A1 * | 10/2016 | Seaman | A61F 5/56 |
| 2017/0028162 | A1 * | 2/2017 | Leeflang | A61M 16/0616 |
| 2017/0080207 | A1 * | 3/2017 | Perez | A61F 5/0003 |
| 2018/0000696 | A1 | 1/2018 | Villeneuve et al. | |
| 2021/0106455 | A1 * | 4/2021 | McKeown | A61F 5/56 |

FOREIGN PATENT DOCUMENTS

| | | |
|---|---|---|
| JP | 2014236928 A | 12/2014 |
| WO | 2018156762 A1 | 8/2018 |
| WO | 2019098621 A1 | 5/2019 |

* cited by examiner

NASAL BREATHING TRAINING TAPE AND METHOD

FIELD OF THE INVENTION

The present invention generally relates to training equipment, and, more particularly, to a training equipment that imparts training to kids to breathe from the nasal, and not from the mouth, during sleep time or wake-up time.

BACKGROUND OF THE INVENTION

More often than not, human being, particularly kids and teens, have a natural tendency to breathe from their mouth rather than their nose, during wake-up time while performing various day to day activities, such as playing, siting, watching televisions or during sleep. Breathing through mouth in not natural and can causes various problems to children or to adults as well. For example, mouth breathing can cause crooked teeth, facial deformities, or poor growth to children, or in adults, chronic mouth breathing can cause bad breath, gum disease, and can worsen symptoms of other illnesses.

If not many, some efforts have been made in past to encourage nasal breathing through various devices. For example, one such device is disclosed in WO Application Number WO2019098621A1. In WO2019098621A1, a lip sealing tape is provided wherein such tap seals the upper and the lower lips to prevent the opening of the lips during daily life and sleep. With such device, one can image the uncomforted level to the person whose lips are just like sealed and retain its opening even when required. Such devices may not have a practical and long-lasting uses as it forces the user to retain their lips is closely tight manner and not them open even one needs or requires it to open. In such discloses arrangement, the lips can only be opened when the lip sealing tapes are torn by the user.

Another example of such devices can be evident in United State Patent Application Number US20160302961A1. US20160302961A1 provides an oral occlusion device for the treatment of respiratory disturbance. Such device provides a central non-adhesive area, which still coves the lip portion of the user causing more or less same difficulties as discussed above in relation to the WO Application Number WO2019098621A1.

As one can evident, despite various efforts made in past, none of the devices are able to solve the real problem, in spite, these devices force the users to retain their lips in locked position, even if the user indent to open it while the device is worn long the lips. Most importantly, none of the devices encourage to impart training skills to breadth from the nasal, rather these devices force users to breadth from the nasal.

Accordingly, there exists a need to impart training skills to kids, teen or adults to breathe from the nasal, and not from the mouth, during sleep time or wake-up time.

SUMMARY OF THE INVENTION

In view of the foregoing disadvantages inherent in the prior art, the general purpose of the present invention is to provide a nasal breathing training tape and method to include all advantages of the prior art, and to overcome the drawbacks inherent in the prior art.

An object of the present disclosure is to impart training skills to kids, teen or adults to breathe from the nasal, and not from the mouth, during sleep time or wake-up time.

With that regard, in one aspect of the present invention, a nasal breathing training tape is provided. The nasal breathing training tape adapted to impart training to a user to breathe from the nasal, and not from the mouth, during sleep time or wake-up time. The nasal breathing training tape includes a stretchable strip, an adhesive layer, and a cutout portion. The stretchable strip includes a first surface, and a second surface opposite to the first surface. The stretchable strip is stretchable to create tension therein. Further, the adhesive layer may be applied to the second layer of the stretchable strip. Furthermore, the cutout portion is configured on the stretchable strip along a substantially central location of the stretchable strip. The stretchable strip is stretched up to a size to be accommodated and stick around a lip portion, surrounding the mouth but not touching the lip portion, of the user, such that the lip portion held together by the tension created in the stretchable strip. Further, due to the tension created by the nasal breathing training tape, an overall neuro-sensory-motor system of the user is stimulated, so that the brain of the user learns to 'switch on' the nasal breathing, when the lip portion is gently held together by the stretchable strip.

In another aspect of the present invention, a method for imparting training to a user to breathe from the nasal, and not from the mouth, during sleep time or wake-up time is provided. The method includes stretching a stretchable strip of a nasal breathing training tape up to a size to be accommodated around a lip portion of the user, and to create tension therein. The stretchable strip includes a cutout portion configured on the stretchable strip along a substantially central location of the stretchable strip. Further, the method includes sticking the stretched stretchable strip, via an adhesive layer applied to a second layer, opposite to a second layer of the stretchable strip, around the lip portion, surrounding the mouth but not touching the lip portion, of the user, such that the lip portion held together by the tension created in the stretchable strip. Due to the tension created by the nasal breathing training tape, an overall neuro-sensory-motor system of the user is stimulated, so that the brain of the user learns to 'switch on' the nasal breathing, when the lip portion is gently held together.

This together with the other aspects of the present invention, along with the various features of novelty that characterize the present invention, is pointed out with particularity in the claims annexed hereto and forms a part of the present invention. For a better understanding of the present invention, its operating advantages, and the specified object attained by its uses, reference should be made to the accompanying drawings and descriptive matter in which there are illustrated exemplary embodiments of the present invention.

BRIEF DESCRIPTION OF THE DRAWINGS

The advantages and features of the present invention will become better understood with reference to the following detailed description and claims taken in conjunction with the accompanying drawings, wherein like elements are identified with like symbols, and in which:

FIG. 2A illustrates top view of the nasal breathing training tape, FIG. 2B illustrates back view of the nasal breathing training tape with an adhesive layer, and FIG. 2C illustrates back view of the nasal breathing training tape with a layer covering the adhesive layer, in accordance with an exemplary embodiment of the present disclosure;

Like reference numerals refer to like parts throughout the description of several views of the drawings.

DETAILED DESCRIPTION OF THE INVENTION

Figure 1:
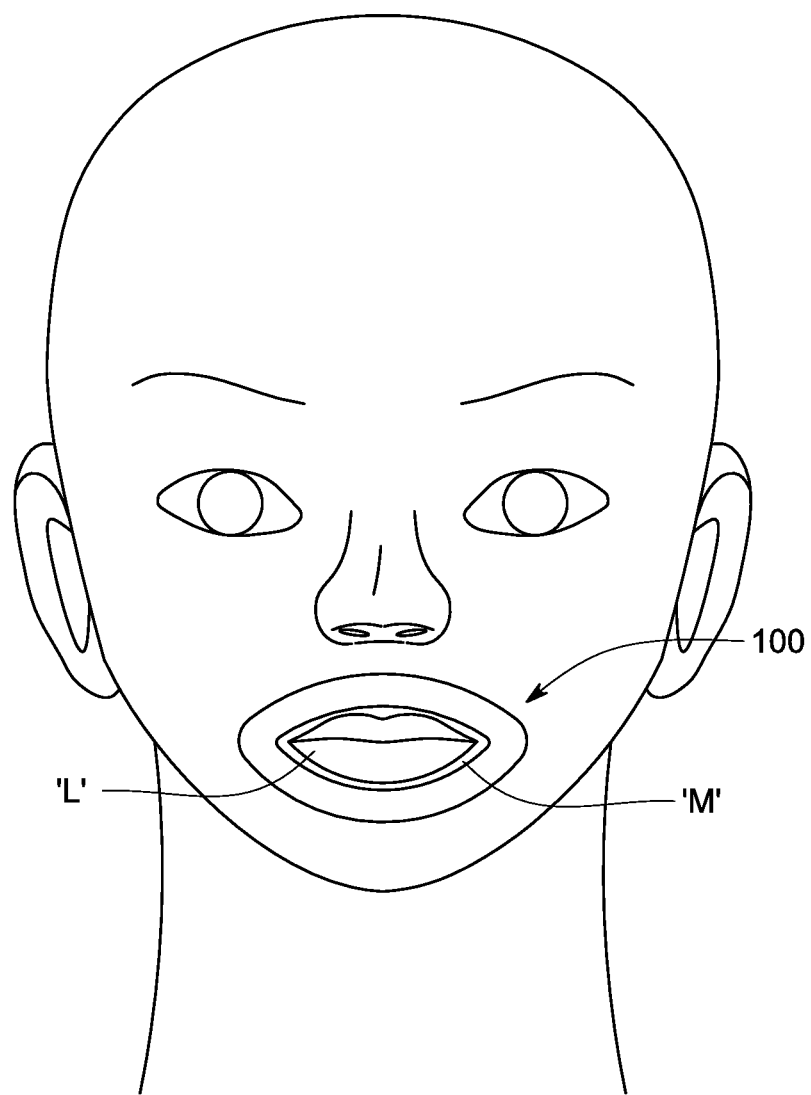
FIG. 1 illustrates an environment wherein a nasal breathing training tape is shown to be incorporated along the users' mouth to impart training to a user to breathe from the nasal, and not from the mouth, during sleep time or wake-up time, in accordance with an exemplary embodiment of the present disclosure.

For a thorough understanding of the present invention, reference is to be made to the following detailed description, including the appended claims, in connection with the above-described drawings. Although the present invention is described in connection with exemplary embodiments, the present invention is not intended to be limited to the specific forms set forth herein. It is understood that various omissions and substitutions of equivalents are contemplated as circumstances may suggest or render expedient, but these are intended to cover the application or implementation without departing from the spirit or scope of the claims of the present invention. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

The terms, "a" and "an" herein do not denote a limitation of quantity, but rather denote the presence of at least one of the referenced items.

The present invention provides a nasal breathing training tape. The nasal breathing training tape adapted to impart training to a user to breathe from the nasal, and not from the mouth, during sleep time or wake-up time. The nasal breathing training tape includes a stretchable strip, an adhesive layer, and a cutout portion. The stretchable strip includes a first surface, and a second surface opposite to the first surface. The stretchable strip is stretchable to create tension therein. Further, the adhesive layer may be applied to the second layer of the stretchable strip. Furthermore, the cutout portion is configured on the stretchable strip along a substantially central location of the stretchable strip. The stretchable strip is stretched up to a size to be accommodated and stick around a lip portion, surrounding the mouth but not touching the lip portion, of the user, such that the lip portion held together by the tension created in the stretchable strip. Further, due to the tension created by the nasal breathing training tape, an overall neuro-sensory-motor system of the user is stimulated, so that the brain of the user learns to 'switch on' the nasal breathing, when the lip portion is gently held together by the stretchable strip.

The present invention also provides a method for imparting training to a user to breathe from the nasal, and not from the mouth, during sleep time or wake-up time. The method includes stretching a stretchable strip of a nasal breathing training tape up to a size to be accommodated around a lip portion of the user, and to create tension therein. The stretchable strip includes a cutout portion configured on the stretchable strip along a substantially central location of the stretchable strip. Further, the method includes sticking the stretched stretchable strip, via an adhesive layer applied to a second layer, opposite to a second layer of the stretchable strip, around the lip portion, surrounding the mouth but not touching the lip portion, of the user, such that the lip portion held together by the tension created in the stretchable strip. Due to the tension created by the nasal breathing training tape, an overall neuro-sensory-motor system of the user is stimulated, so that the brain of the user learns to 'switch on' the nasal breathing, when the lip portion is gently held together.

Referring now to FIG. 1, that illustrates an environment wherein a nasal breathing training tape 100 is shown to be incorporated along a user's mouth 'M' to impart training to the user to breathe from the nasal, and not from the mouth, during sleep time or wake-up time, in accordance with an exemplary embodiment of the present disclosure. Specifically, nasal breathing training tape 100 may be stretched up to a size to be accommodated and stick around a lip portion 'L', surrounding the mouth 'M' but spaced from and not touching the lip portion 'L', of the user, as shown in FIG. 1, such that the lip portion 'L' held together.

Figure 2A:
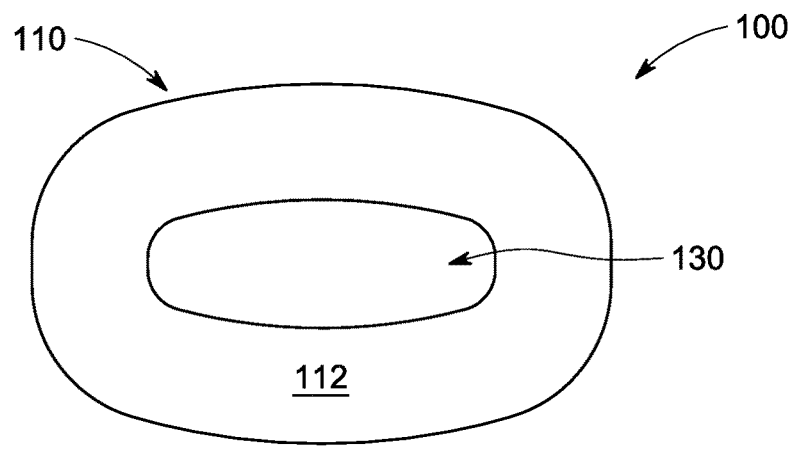
FIGS. 2A to 2C illustrate various views of a nasal breathing training tape, i.e.
Figure 2B:
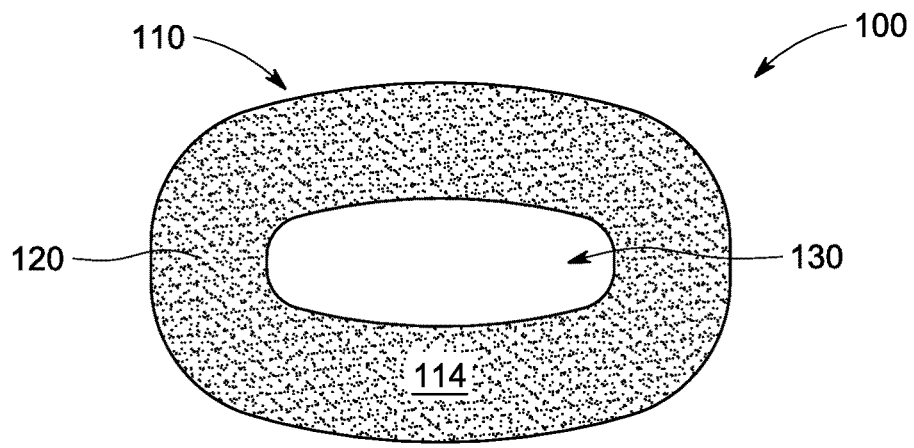
Figure 2C:
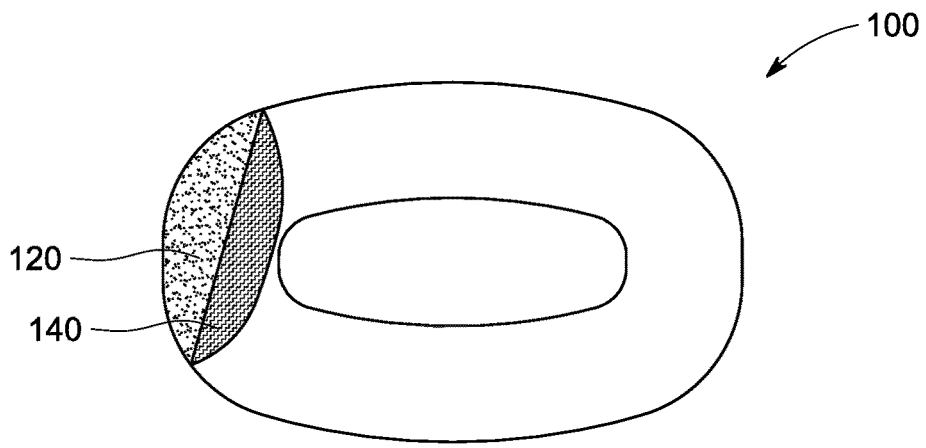

Referring now to FIGS. 2A to 2C, various views of the nasal breathing training tape 100, in accordance with an exemplary embodiment of the present disclosure are shown and now will be explained in conjunction to FIG. 1. In one example embodiment, as shown in FIGS. 2A to 2C, the nasal breathing training tape 100 may include a stretchable strip 110, an adhesive layer 120, and a cutout portion 130. The stretchable strip 110 may include a first surface 112, and a second surface 114 opposite to the first surface 112. The stretchable strip 110 may be stretchable to create tension therein. Further, the adhesive layer 120 may be applied to the second layer 114 of the stretchable strip 100. Furthermore, the cutout portion 130 may be configured on the stretchable strip 110 along a substantially central location of the stretchable strip 110. In one embodiment, the cutout portion 130 generally corresponds to the lip portion 'L', such that the lip portion 'L' protrudes from the cutout portion 130, as shown in FIG. 1.

The stretchable strip 110 may be stretched up to a size to be accommodated and stick around the lip portion 'L', surrounding the mouth 'M' but not touching the lip portion 'L', of the user, such that the lip portion 'L' held together by the tension created in the stretchable strip 110. Further, due to the tension created by the nasal breathing training tape 100, an overall neuro-sensory-motor system of the user is stimulated, so that the brain of the user learns to 'switch on' the nasal breathing, when the lip portion 'L' are gently held together by the stretchable strip 110.

In one embodiment, the stretchable strip 110 may be made of a cotton material or a synthetic material that has stretchable property therein. However, without departing from the scope of the present disclosure, the stretchable strip 110 may be made of any other suitable material having stretchable property. In one preferred embodiment of the present disclosure, the stretchable strip 110 may include a property of stretchability of about 20% to about 30%. For example, the stretchable strip 110 may be stretched up to about 20% to about 30% of its actual size to create tension in the stretchable strip 110. The adhesive layer 120 also retains its adhesiveness when the stretchable strip 110 is stretched up to about 20% to 30%. In one example, a perfect stretch for the stretchable strip 110 of about 54 mm may be about 65 mm, at which the adhesiveness of the adhesive layer 120 is also effectively retained.

Figure 4:
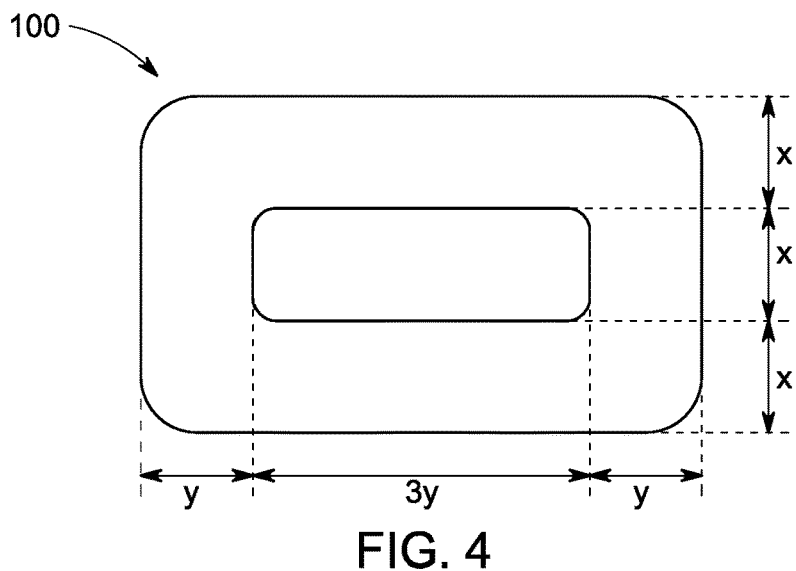
FIG. 4 illustrates an example of shape and dimensional measurement of a nasal breathing training tape, in accordance with another exemplary embodiment of the present disclosure.

In one further embodiment, the stretchable strip 110 may be of one of a rectangular shape or of an elliptical shape. One example depiction of the elliptical shape of the stretchable strip is shown in FIGS. 2A to 2C. However, the stretchable strip 110 may also be of the rectangular shape, such as shown in FIG. 4. The stretchable strip 110 where its shape is rectangular, the corners thereof may be rounded, as shown in FIGS. FIG. 4. Further, the cutout portion 130 may also correspond to the shape of the stretchable strip 110, and may be one of a rectangular shape, as shown in FIG. 4, and may be of an elliptical shape, as shown in FIGS. 2A-2C. As described, the stretchable strip 110 where its shape is rectangular, the corners thereof are rounded. Similarly, where the shape of the cutout portion 130 is having the rectangular shape, the corners thereof may also be rounded, as shown in FIGS. FIG. 4. As shown in FIGS. 2A-2C or FIG. 4, the shape of the stretchable strip 110 and the cutouts 130 shown to be elliptical or rectangular, are for better understanding of the present invention, and that the shape of the stretchable strip 110 and the cutouts 130 may not considered to be limiting in any manner only to elliptical or rectangular. The disclosure, without departing from the scope of the present disclosure, intend to cover various other shapes, such as circular or square and so forth.

Figure 3:
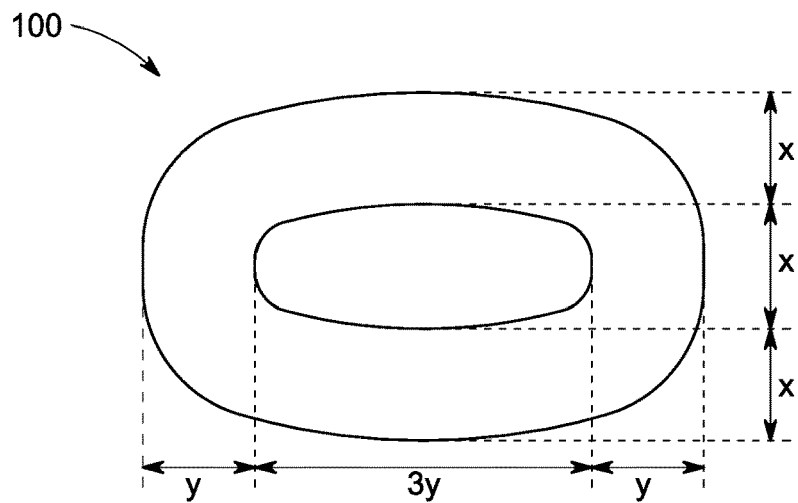
FIG. 3 illustrates an example of dimensional measurement of a nasal breathing training tape, in accordance with an exemplary embodiment of the present disclosure.

In one further embodiment, the stretchable strip 110 comprises a predetermined shape having a width and a length, wherein a ratio of width to length is about 3:5. For example, as shown in FIG. 3, the stretchable strip 110 has a predetermined shape of an ellipse having a width of 3x and a length of 5y, wherein x=y=1. Another example is shown in FIG. 4, where the stretchable strip 110 has a predetermined shape of a rectangle having a width of 3x and a length of 5y, wherein x=y=1. In One example, the stretchable strip 110 may have a length of about 54 mm and a width of about 33 mm. In one another example, the stretchable strip 110 may have a width of about 30 mm and the length of about 50 mm.

In one further embodiment, a ratio of the cutout portion 130 to the stretchable strip 110 may be about 1:3, without departing from the scope of the present disclosure. For example, if the stretchable strip 110 is having a length of 5y and width of 3x; then the cutout portion 130 may be of 1x in width and 3y in length, wherein x=y=1. In further example, if the stretchable strip 110 is having a length of about 54 mm and a width of about 33 mm, then the cutout portion 130 may have a length of about 32 mm and a width of about 11 mm. In further example, if the stretchable strip 110 is having a width of about 30 mm and the length of about 50 mm, then the cutout portion 130 may have a length of about 30 mm and a width of about 10 mm.

Figure 5:
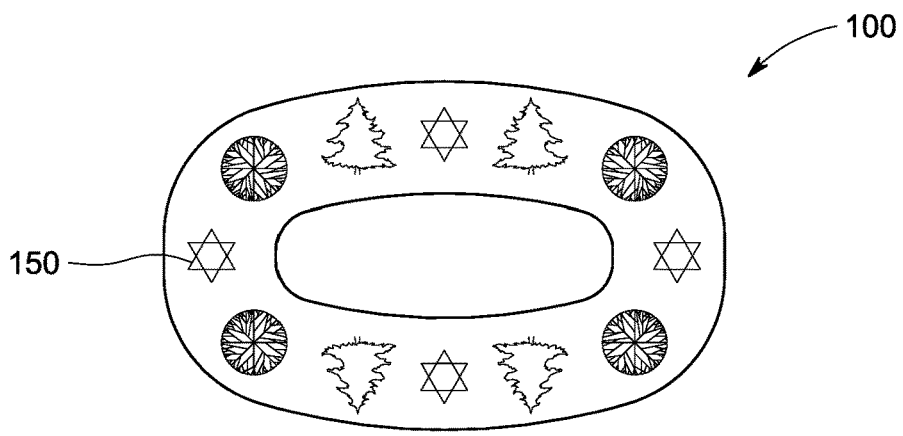
FIG. 5 illustrates a nasal breathing training tape having patters, in accordance with another exemplary embodiment of the present disclosure.

In one further embodiment, the stretchable strip 110 may include one or more patterns of cartoon characters, or, one or more universal characters including cars, stars, moon, sun, flowers, and so forth, as shown in FIG. 5. Particularly, the first surface 112 of the stretchable strip 110 may include such cartoon characters and/or universal characters. Such cartoon characters and/or universal characters may make the nasal breathing training tape 100 attractive to kids and kids may get encouraged to stick such nasal breathing training tape for training purpose.

In one embodiment, as mentioned above, the adhesive layer 120 may be applied to the second layer 114 of the stretchable strip 110. The adhesive in the adhesive layer 120 is such that it is adaptable to human skin. In one embodiment, as shown in FIG. 2B, the nasal breathing training tape 100 may be directly stretched and stick to surrounding of the mouth 'M' but not touching the lip portion 'L', with the help of an exposed adhesive layer 120. Such adhesive may retain its adhesiveness upon applying a liquid to the adhesive layer 120. However, in another embodiment, as shown in FIG. 2C, the adhesive layer 120 may be covered by another layer, such as layer 140, made of paper or plastic. In this embodiment, the user may remove the layer 140 to expose the adhesive layer 120. Upon exposure of the adhesive layer 120, the nasal breathing training tape 100 may be directly stretched and stick to surrounding of the mouth 'M' but not touching the lip portion 'L'.

Figure 6:
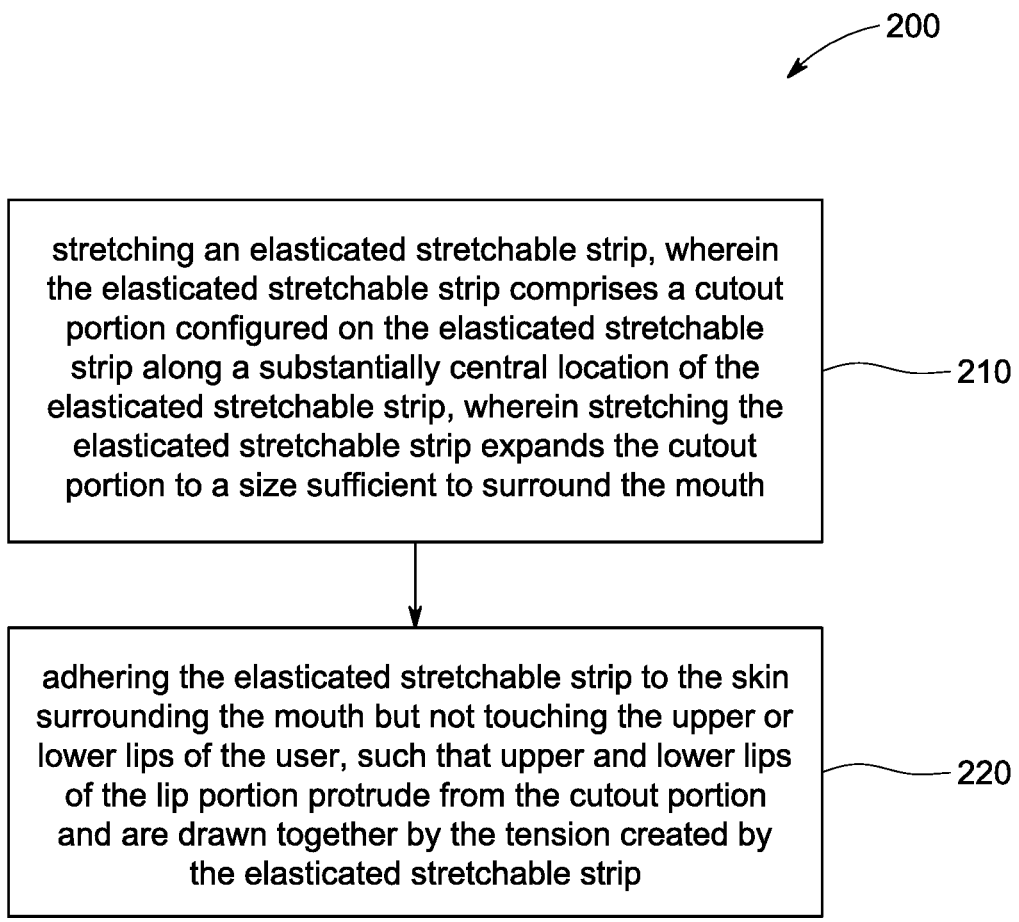
FIG. 6 illustrates a flow chart of a method of using a nasal breathing training tape, in accordance with another exemplary embodiment of the present disclosure.

Referring now to FIG. 6, a method 200 for imparting training to the user to breathe from the nasal, and not from the mouth, during sleep time or wake-up time is provided. The method 200, at step 210 stretch the stretchable strip 110 of the nasal breathing training tape 100 up to a size to be accommodated around a lip portion of the user, and to create tension therein. In one embodiment, the stretchable strip may be stretched from about 20% to about 30%. The stretchable strip 110 is excluded herein from explanation for the sake of brevity. Further, the method 200, at step 220, includes sticking the stretched stretchable strip, via the adhesive layer 120, surrounding the mouth but not touching the lip portion, of the user, such that the lip portion held together by the tension created in the stretchable strip 110. Due to the tension created by the nasal breathing training tape 100, an overall neuro-sensory-motor system of the user is stimulated, so that the brain of the user learns to 'switch on' the nasal breathing, when the lip portion is gently held together. In one embodiment, the nasal breathing training tape 100 may be worn during the day for about 30 minutes to two hours, especially while child is distracted. The nasal breathing training tape 100 may also be worn during sleep.

The present invention provides a nasal breathing training tape, such as the nasal breathing training tape 100, which offers the various advantages. Most importantly, the nasal breathing training tape 100 imparts training skills to kids, teen or adults to breathe from the nasal, and not from the mouth, during sleep time or wake-up time. The nasal breathing training tape is placed surrounding the lips, but not in direct contact with the lips. The nasal breathing training tape may be made from cotton or synthetic materials to stretch in two or four ways. Due to the tension created by the nasal breathing training tape, the overall neuro-sensory-motor system is stimulated, so that the brain learns to 'switch on' nasal breathing when the lips are gently held together. The nasal breathing training tape stimulates the skin, which is regulated by the trigeminal, which sandwiches the perioral muscles, including the orbicularis oris regulated by the facial muscles. The purpose of the nasal breathing training tape is to re-educate children and teenagers to nasal breathe. The nasal breathing training tape should be worn during the day for 30 minutes to two hours, especially while child is distracted. The tape may also be worn during sleep.

The foregoing descriptions of specific embodiments of the present invention have been presented for purposes of illustration and description. They are not intended to be exhaustive or to limit the present invention to the precise forms disclosed, and obviously many modifications and variations are possible in light of the above teaching. The embodiments were chosen and described in order to best explain the principles of the present invention and its practical application, to thereby enable others skilled in the art to best utilize the present invention and various embodiments with various modifications as are suited to the particular use contemplated. It is understood that various omission and substitutions of equivalents are contemplated as circumstance may suggest or render expedient, but such are intended to cover the application or implementation without departing from the spirit or scope of the claims of the present invention.

What is claimed is:

1. A method for imparting training to a user to breathe from the nasal, and not from the mouth, during sleep time or wake-up time, the method comprising:

stretching a stretchable strip of a nasal breathing training tape comprising (i) an upper lip portion, (ii) a lower lip portion, (iii) a left side portion and (iv) a right side portion up to a size to be accommodated around lips of the user, and to create tension therein, the stretchable strip comprising cotton material or a synthetic material that has stretchable property, and having a cutout portion on the stretchable strip along a central location of the stretchable strip in which an area ratio of the cutout portion in the stretchable strip is 1:3, wherein a ratio of width to length of the stretchable strip is 3:5; and sticking the stretched stretchable strip, via an adhesive layer applied to a first layer, opposite to a second layer of the stretchable strip, around the lips, surrounding the mouth such that the nasal breathing training tape is spaced from and not touching the lips, of the user, such that the lips are held together by the tension created in the stretchable strip;

whereby due to the tension created by the nasal breathing training tape, an overall neuro-sensory-motor system of the user can be stimulated, so that the brain of the user can learn to 'switch on' the nasal breathing when the lips are gently held together, and wherein the cutout portion is void of any material.

2. The method of claim 1, further including stretching the stretchable strip 20% up to 30%.

3. The method of claim 1, further including sticking the stretched stretchable strip for 30 minutes to 2 hours.

4. The method of claim 1, wherein the stretchable strip comprises one of a rectangular shape and an elliptical shape, wherein the stretchable strip with the rectangular shape having rounded corners.

5. The method of claim 1, wherein a first surface of the stretchable strip comprises one or more patterns of cartoon characters, or one or more characters including cars, stars, moon, sun, flowers.

6. The method of claim 1, wherein the cutout portion is adapted to correspond to the lips such that the lips are configured to protrude from the cutout portion.

7. The method of claim 1, wherein the cutout portion comprises one of a rectangular shape and an elliptical shape, wherein the cutout portion with the rectangular shape comprises rounded corners.

* * * * *